US006934586B2

(12) United States Patent
Struble et al.

(10) Patent No.: US 6,934,586 B2
(45) Date of Patent: Aug. 23, 2005

(54) CARDIAC RESYNCHRONIZATION WITH ADAPTIVE A1-A2 AND/OR V1-V2 INTERVALS

(75) Inventors: Chester Struble, Eijsden (NL); Pierre Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 306 days.

(21) Appl. No.: 10/127,037

(22) Filed: Apr. 22, 2002

(65) Prior Publication Data

US 2003/0199934 A1 Oct. 23, 2003

(51) Int. Cl.⁷ .............................................. A61N 1/365
(52) U.S. Cl. ...................................... 607/23; 607/18
(58) Field of Search ........................... 607/9, 17–18, 607/23

(56) References Cited

U.S. PATENT DOCUMENTS

| | | | |
|---|---|---|---|
| 4,316,472 A | 2/1982 | Mirowski et al. ............... 607/9 |
| 4,375,817 A | 3/1983 | Engle et al. .................... 607/4 |
| 4,379,459 A | 4/1983 | Stein ............................... 607/9 |
| 4,476,868 A | 10/1984 | Thompson .................... 607/14 |
| 4,485,813 A | 12/1984 | Anderson et al. ............ 600/488 |
| 4,566,063 A | 1/1986 | Thompson ..................... 712/241 |
| 4,587,970 A | 5/1986 | Holley et al. .................. 607/15 |
| 4,726,380 A | 2/1988 | Vollmann et al. .............. 607/15 |
| 4,727,877 A | 3/1988 | Kallok ............................. 607/5 |
| 4,800,883 A | 1/1989 | Winstrom ....................... 607/7 |
| 4,821,723 A | 4/1989 | Baker et al. ..................... 607/7 |
| 4,880,005 A | 11/1989 | Pless et al. ................... 607/15 |
| 4,949,719 A | 8/1990 | Pless et al. ..................... 607/7 |
| 4,953,551 A | 9/1990 | Mehra et al. .............. 122/18.4 |
| 5,099,838 A | 3/1992 | Bardy ............................ 607/2 |
| 5,131,388 A | 7/1992 | Pless ............................... 607/5 |
| 5,144,949 A | 9/1992 | Olson et al. .................. 607/17 |
| 5,158,078 A | 10/1992 | Bennett et al. ................ 607/27 |
| 5,163,427 A | 11/1992 | Keimel ............................ 607/5 |
| 5,163,429 A * | 11/1992 | Cohen ............................. 607/4 |
| 5,168,869 A | 12/1992 | Chirife ........................... 607/25 |
| 5,199,428 A | 4/1993 | Obel et al. ..................... 607/44 |
| 5,207,218 A | 5/1993 | Carpenter et al. ............ 607/36 |
| 5,269,298 A | 12/1993 | Adams et al. .................. 607/5 |
| 5,312,453 A | 5/1994 | Shelto et al. ................. 607/19 |
| 5,314,430 A | 5/1994 | Bardy ............................. 607/5 |
| 5,330,507 A | 7/1994 | Schwortz ...................... 607/14 |
| 5,331,966 A | 7/1994 | Bennet et al. .............. 600/508 |
| 5,354,316 A | 10/1994 | Keimel ......................... 607/15 |
| 5,545,186 A | 8/1996 | Olson et al. .................. 607/14 |
| 5,690,886 A | 11/1997 | Kurihara ................ 264/328.12 |
| 6,070,101 A | 5/2000 | Struble et al. .................. 607/9 |
| 6,081,748 A | 6/2000 | Struble et al. .................. 607/9 |
| 6,122,545 A | 9/2000 | Struble et al. .................. 607/9 |
| 6,144,880 A | 11/2000 | Ding et al. ................... 607/23 |
| 6,567,700 B1 * | 5/2003 | Turcott et al. ................. 607/9 |
| 6,666,826 B2 * | 12/2003 | Salo et al. ................... 600/485 |
| 6,738,667 B2 * | 5/2004 | Deno et al. .................. 607/23 |

FOREIGN PATENT DOCUMENTS

WO WO92/8198 5/1992 ........... G06F/15/20

OTHER PUBLICATIONS

"Automatic Tachycardia Recognition" by Arzbaecher et al. PACE May–Jun. 1984, pp. 541–547.

* cited by examiner

Primary Examiner—Carl Layno
(74) Attorney, Agent, or Firm—Girma Wolde-Michael; Paul H. McDowall

(57) ABSTRACT

In a system that provides bi-atrial and/or bi-ventricular pacing, the system adjusts an interval between paces delivered to the atria, and/or an interval between paces delivered to the ventricles, as a function of pressure data from the heart. In an exemplary embodiment, the system uses the pressure data from the ventricles to identify the times that each ventricle begins ejection of blood. The system may adjust the interval between paces to cause the ventricles to begin ejection at the same time, or to cause one ventricle to commence blood ejection prior to the other ventricle with a desired time offset. The system may further adjust the interval in response to changing conditions, such as a changing heart rate.

63 Claims, 10 Drawing Sheets

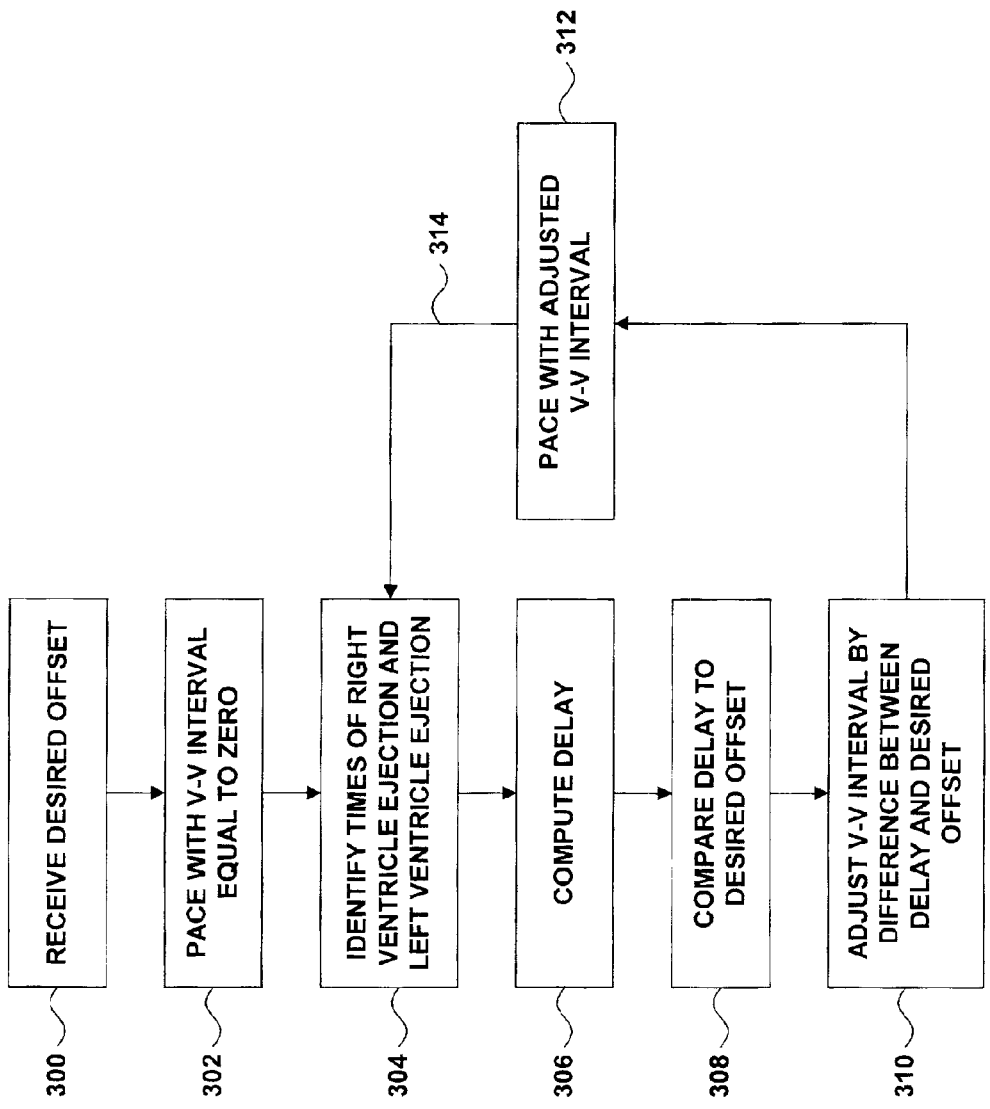

CARDIAC RESYNCHRONIZATION WITH ADAPTIVE A1-A2 AND/OR V1-V2 INTERVALS

FIELD OF THE INVENTION

The invention relates to cardiac pacing systems, and more particularly to multiple-chamber cardiac pacing systems.

BACKGROUND

Many patients that suffer from congestive heart failure (CHF) develop a wide QRS complex resulting from a delayed activation of one of the ventricles in the heart, and inter- and/or intraventricular electrical-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at significantly different times. The timing imbalance may also cause the patient to experience paradoxical septal motion, mitral regurgitation or decreased ventricular filling time.

Patients having a wide QRS complex or having inter- and/or intraventricular electrical-mechanical dysynchrony may receive benefits from an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with one or more pacing leads in two or more complementary chambers of the heart. For purposes of the following discussion, the right and left atria are complementary to one another, and the right and left ventricles are complementary chambers. The right and left atria are complementary because they are the upper chambers that receive blood and transfer it to the ventricles. The right and left ventricles are complementary chambers because they receive blood from the atria and pump the blood to the heart. In a heart in a healthy patient, complementary chambers activate at approximately the same time. In a heart in a patient suffering from a condition such as CHF, complementary chambers activate at different times.

In response to a sensed or paced event, the pacemaker delivers pacing pulses or stimulations to two complementary chambers of the heart. The pacing pulses may be, but need not be, delivered simultaneously. Although the discussion that follows emphasizes bi-ventricular pacing to treat ventricular dysynchrony, cardiac resynchronization also encompasses, for example, resynchronization of atrial contractions.

Multiple-chamber pacing systems in general, and bi-ventricular and bi-atrial pacing systems in particular, are known in the art. Prior art techniques for synchronizing ventricles or atria are generally imprecise, however, and are not adaptive to changing conditions. In a typical bi-ventricular pacemaker that delivers pacing pulses to the ventricles at different times, for example, the time interval between delivery of the pacing pulses may be fixed and not automatically adjustable.

Examples of these techniques and/or devices may be found in the issued U.S. patents listed in Table 1 below.

TABLE 1

| U.S. Pat. No. | Inventor | Issue Date |
| --- | --- | --- |
| 4,485,813 | Anderson et al. | Dec. 4, 1984 |
| 5,158,078 | Bennett et al. | Oct. 27, 1992 |
| 6,070,101 | Struble et al. | May. 30, 2000 |
| 6,081,748 | Struble et al. | Jun. 27, 2000 |
| 6,122,545 | Struble et al. | Sep. 19, 2000 |
| 6,144,880 | Ding et al. | Nov. 7, 2000 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to multiple chamber cardiac pacemakers in general, and bi-ventricular cardiac pacemakers in particular. These problems include, for example, an inability to adapt a pacing interval to current cardiac conditions to promote hemodynamic efficiency, and an inability to adapt a pacing interval to changing cardiac conditions. Various embodiments of the present invention have the object of solving at least one of the foregoing problems.

It is an object of the invention to select a time interval separating pacing pulses to the ventricles or the atria that promotes hemodynamic efficiency. In a typical embodiment described below, the invention may be applied to bi-ventricular pacing. In this application, the interval may be called the "V1-V2 interval," which represents the time delay between delivery of pacing pulses to the ventricles. In some patients, simultaneous stimulation of the ventricles results in a lack of mechanical ventricular synchrony. The lack of synchrony may be caused by factors such as differences in placement of stimulating electrodes proximate to the ventricles or the differences in the conductive pathways of the ventricles. The lack of synchrony may cause the ventricles to begin ejection of blood at different times. For some patients, asynchronous blood ejection is inefficient and undesirable. The techniques of the invention bring the ventricles into synchrony, resulting in improved hemodynamic performance.

It is a further object of the invention that the techniques be adaptable to bi-atrial pacing. Accordingly, the techniques of the invention may also be applied to set or reset the "A1-A2 interval," which represents the time delay between delivery of pacing pulses to the atria. Another object of the invention is that the techniques be adaptable to patients who need both bi-atrial pacing and bi-ventricular pacing. Accordingly, the techniques of the invention may be applied to both the A1-A2 interval and the V1-V2 interval employed by a four-chamber pacemaker.

An additional object of the invention is that cardiac resynchronization may be performed automatically. In particular, pacing intervals such as the V1-V2 interval may be set to improve the hemodynamic efficiency of the heart of a patient, and may be reset in response to changing conditions. The invention presents techniques for resynchronizing cardiac chambers in response to changes in heart rate, for example.

Various embodiments of the invention may possess one or more features capable of fulfilling the above objects. In general, the invention includes a pacemaker that provides multi-chamber pacing. In a typical embodiment, the pacemaker may provide pacing stimuli to both ventricles of a heart. The invention may also include sensors that collect pressure data, such as pressure data from the left ventricle and the right ventricle. The pressure data may be used to identify an event in the cardiac cycle for the two complementary chambers, such as the time at which each chamber begins ejecting blood. The invention may also include a processor that computes an interval such that pacing pulses, separated by this interval, cause the chambers to work in synchrony. In a typical application, the processor may set the interval to cause the right and left ventricles to commence blood ejection at the same time. In another application, the processor may set the interval to cause one ventricle to commence blood ejection prior to the other ventricle with a desired time offset. The processor may further adjust the interval in response to changing conditions, such as a changing heart rate.

The invention may offer one or more advantages. By selection of an interval that separates pacing pulses delivered to the ventricles or to the atria, the chambers of the heart may be synchronized for near-optimal cardiac performance. When the chambers are synchronized, the patient may experience improved cardiac performance, such as improved stroke volume and cardiac output. Moreover, the chambers of the heart may be resynchronized for near-optimal cardiac performance in response to changing conditions.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 10 is a flow diagram illustrating exemplary techniques for setting a V1-V2 interval in response to pressure measurements.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
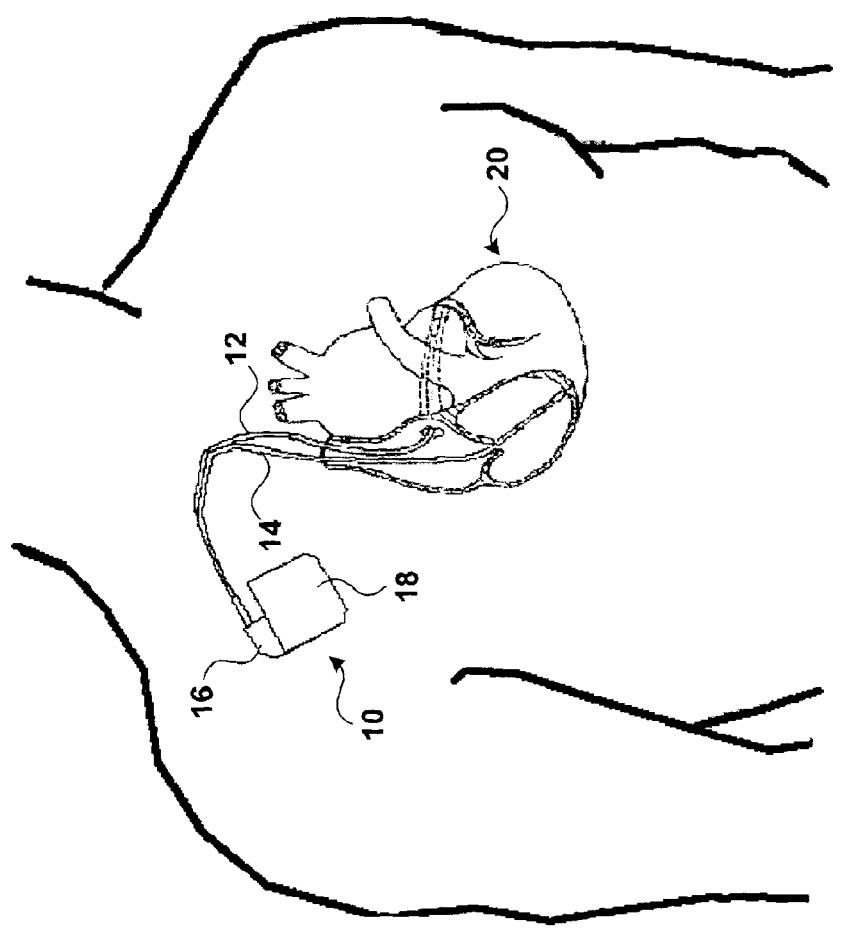
FIG. 1 is a schematic view of an exemplary implantable medical device.

FIG. 1 is a simplified schematic view of one embodiment of implantable medical device (IMD) 10 of the present invention. IMD 10 shown in FIG. 1 is a pacemaker comprising at least one pacing and/or sensing leads 12 attached to connector module 14 of hermetically sealed housing 16 and implanted near human or mammalian heart 20. Pacing and sensing lead 12 senses electrical signals attendant to the depolarization and re-polarization of heart 20, and further provide pacing pulses for causing depolarization of cardiac tissue in the vicinity of the distal ends thereof. Lead 12 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Lead 12 may also include one or more pressure sensors that respond to the absolute pressure inside heart 20. As will be described in more detail below, the pressure sensor may generate pressure signals or may modulate pressure signals conducted through lead 12. The pressure signals may be received by IMD 10.

Figure 2:
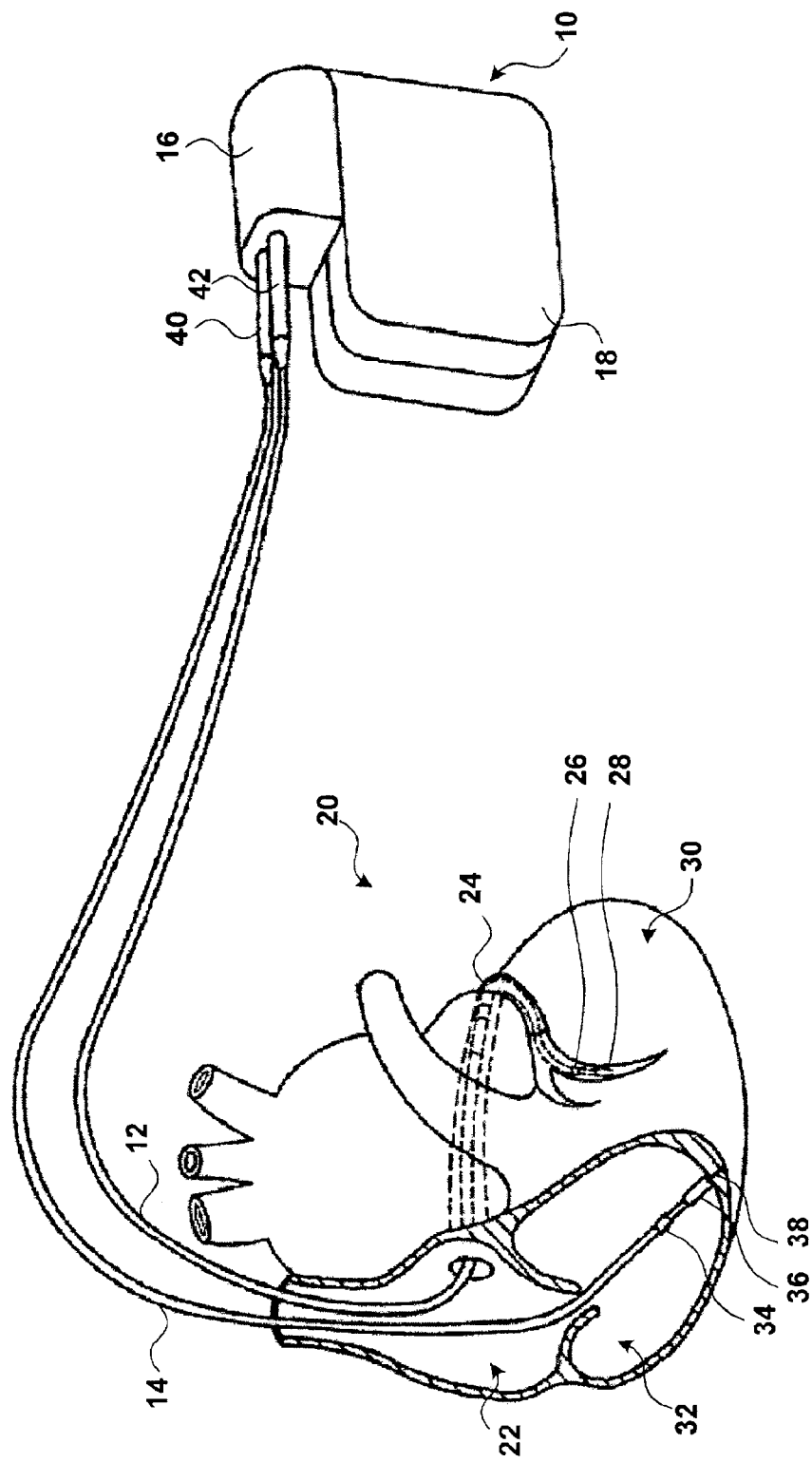
FIG. 2 shows the exemplary implantable medical device of FIG. 1 located in and near a heart.

FIG. 2 is a schematic representation of an exemplary implanted, two-channel cardiac pacemaker 10 in which the invention may be practiced. Pacemaker 10 is shown in conjunction with a human heart 20. Bipolar, endocardial left ventricular (LV) coronary sinus lead 12 is passed through a vein into the right atrium 22 of heart 20, into the coronary sinus 24 and then inferiorly in the great vein and cardiac veins extending from coronary sinus 24 to extend the distal ring pace/sense electrodes 26 and 28 alongside the LV chamber 30. The distal end of LV coronary sinus lead 12 positions ring electrodes 26 and 28 optimally with respect to the adjacent wall of left ventricle 30. Bipolar, endocardial right ventricular (RV) lead 14 is passed through the vein into right atrium 22 and into the right ventricle 32 where its distal ring and tip pace/sense electrodes 34 and 36 are fixed in place in the apex or in the interventricular septum by a distal attachment mechanism 38.

Pace/sense electrodes 26, 28, 34 and 38 sense electrical signals attendant to the depolarization and repolarization of heart 20. The electrical signals are conducted to pacemaker 10 via leads 12 and 14. Pace/sense electrodes 26, 28, 34 and 38 further deliver pacing pulses for causing depolarization of cardiac tissue in the vicinity of the distal ends thereof. The pacing pulses are generated by pacemaker 10 and are transmitted to pace/sense electrodes 26, 28, 34 and 38 via leads 12 and 14.

RV lead 14 is formed with an in-line connector 40 fitting into a bipolar bore of pacemaker connector block 16. RV lead 14 includes a pair of electrically insulated conductors that couple distal tip pace/sense electrode 36 and proximal pace/sense ring electrode 34 to pacemaker 10. LV coronary sinus lead 12 is formed with an in-line connector 42 fitting into a bipolar bore of pacemaker connector block 16. LV coronary sinus lead 12 couples distal ring pace/sense electrode 28 and proximal pace/sense ring electrode 26 to pacemaker 10.

Pacemaker 10 may deliver pacing pulses to ventricles 30, 32. Although the pacing pulses may be delivered to both ventricles 30, 32 simultaneously, in many cases there is a delay between delivery of a pacing pulse to one ventricle and a pacing pulse to the other ventricle. This delay is called the V1-V2 interval.

In general, the object of the V1-V2 interval is to promote ventricular synchrony. Due to physiological differences such as differences in conductive paths in ventricles 30, 32, one ventricle may activate before the other when the ventricles are paced at the same time. The V1-V2 interval compensates for the physiological differences. Although the ventricles 30, 32 are paced at different times, they activate together. The hemodynamic performance of heart 20 is enhanced when ventricles 30, 32 activate synchronously.

In general, the invention presents techniques for detecting whether the ventricles are activating synchronously and adjusting the V1-V2 interval to restore synchronous activation. As will be described in more detail below, the invention may also apply to synchronous activation of the atria of heart 20.

The pacing system shown in FIG. 2 is exemplary. The invention is not limited to the electrode placements shown in FIG. 2. LV pace/sense electrodes 26 and 28, for example, may be located at a site other than coronary sinus 24. RV pace/sense electrodes 34 and 36 likewise may be located at a site other than inside right ventricle 32. For example, RV pace/sense electrodes 34 and 36 may be epicardial, rather than endocardial as shown in FIG. 2. The pacing system may also include alternate or additional leads that deploy electrodes elsewhere around ventricles 30, 32, or proximate to the atria for sensing or pacing.

Furthermore, the invention is not limited to the bipolar ventricular lead systems depicted in FIG. 2. The invention may be employed with unipolar lead systems that employ a single pace/sense electrode in the depicted positions proximate to right ventricle 32 and left ventricle 30. Unipolar electrodes may cooperate with a remote electrode formed as part of the outer surface of the hermetically sealed housing 18 of pacemaker 10.

Figure 3:
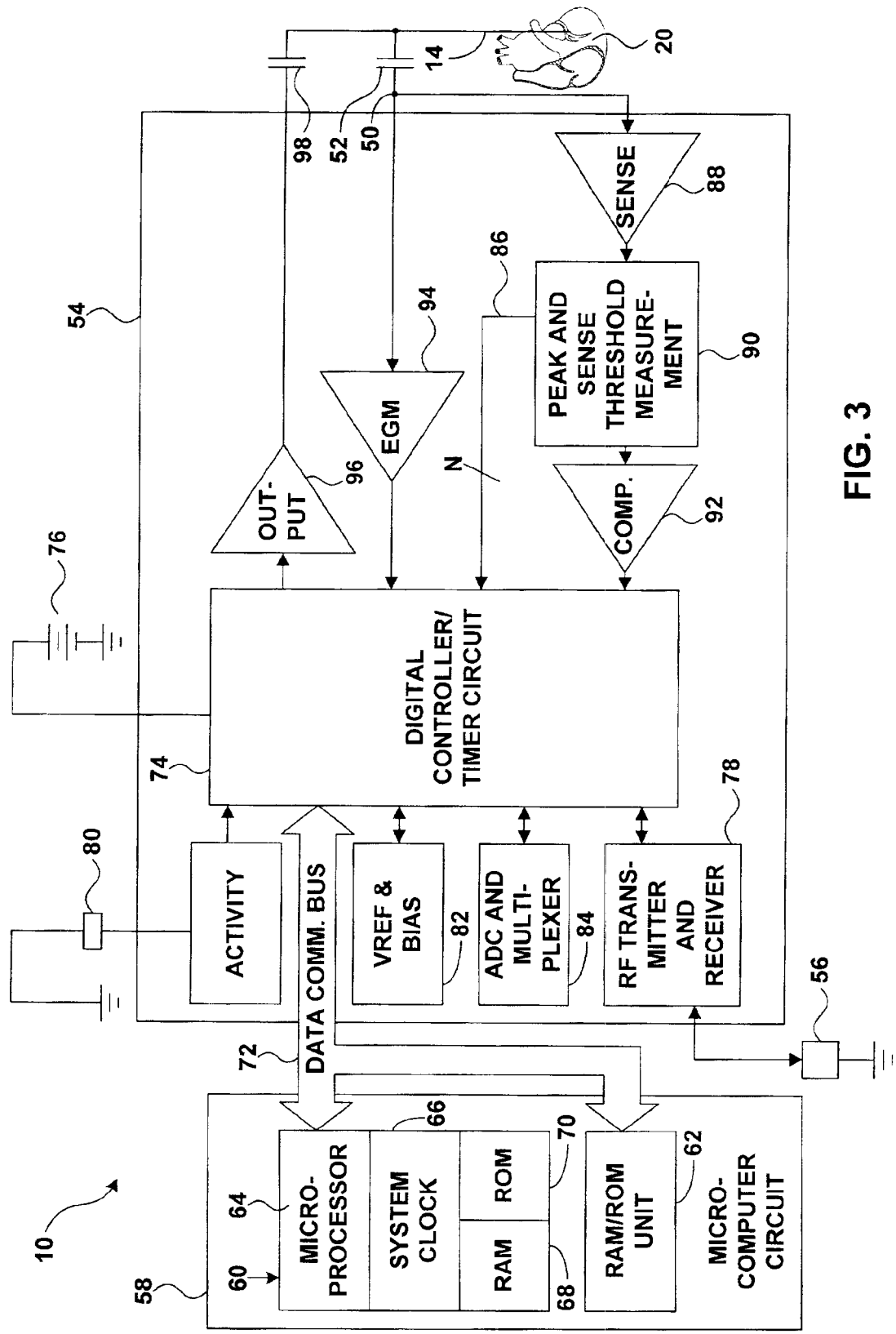
FIG. 3 is a block diagram illustrating the constituent components of the implantable medical device of FIGS. 1 and 2.

FIG. 3 shows a block diagram illustrating the constituent components of pacemaker 10 in accordance with one embodiment of the present invention. Pacemaker 10 is a pacemaker having a microprocessor-based architecture. Pacemaker 10 is shown as including activity sensor or accelerometer 44, which is preferably a piezoceramic accelerometer bonded to a hybrid circuit located inside housing 18 (shown in FIGS. 1 and 2). Activity sensor 44 typically (although not necessarily) provides a sensor output that varies as a function of a measured parameter relating to a patient's metabolic requirements. For the sake of convenience, pacemaker 10 in FIG. 3 is shown with lead 12 only connected thereto. However, it is understood that similar circuitry and connections not explicitly shown in FIG. 3 apply to lead 14 (shown in FIGS. 1 and 2).

Pacemaker 10 in FIG. 3 is most preferably programmable by means of an external programming unit (not shown in the figures). One such programmer is the commercially available Medtronic Model 9790 programmer, which is microprocessor-based and provides a series of encoded signals to pacemaker 10, typically through a programming head which transmits or telemeters radio-frequency (RF) encoded signals to pacemaker 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 12 is coupled to node 50 in pacemaker 10 through input capacitor 52. Activity sensor or accelerometer 44 is most preferably attached to a hybrid circuit located inside hermetically sealed housing 18 of pacemaker 10. The output signal provided by activity sensor 44 is coupled to input/output circuit 54. Input/output circuit 54 contains analog circuits for interfacing with heart 20, activity sensor 44, antenna 56 and circuits for the application of stimulating pulses to heart 20. The rate of heart 20 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of pacemaker 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of pacemaker 10 are coupled from microprocessor 64 via data bus 72 to digital controller/timer circuit 74, where digital timers and counters establish the overall escape interval of the pacemaker 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when pacemaker 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12.

In some preferred embodiments of the present invention, pacemaker 10 may operate in various non-rate-responsive modes. In other preferred embodiments of the present invention, pacemaker 10 may operate in various rate-responsive modes. Some embodiments of the present invention are capable of operating in both non-rate-responsive and rate-responsive modes. Moreover, in various embodiments of the present invention pacemaker 10 may be programmably configured to operate so that it varies the rate at which it delivers stimulating pulses to heart 12 in response to one or more selected sensor outputs being generated. Numerous pacemaker features and functions not explicitly mentioned herein may be incorporated into pacemaker 10 while remaining within the scope of the present invention.

The present invention is not limited in scope to any particular number of sensors, and is not limited to pacemakers comprising activity or pressure sensors only. Although the present invention is useful in multiple-chamber pacemakers, the present invention is not limited in scope to pacemakers having any particular number of sensors per lead. At least some embodiments of the present invention may be applied equally well in the contexts of dual-, triple- or quadruple-chamber pacemakers or other types of pacemakers. See, for example, U.S. Pat. No. 5,800,465 to Thompson et al., hereby incorporated by reference herein in its entirety, as are all U.S. patents referenced therein.

Pacemaker 10 may also be a pacemaker combined with a cardioverter and/or defibrillator. Various embodiments of the present invention may be practiced in conjunction with a pacemaker-cardioverter-defibrillator such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
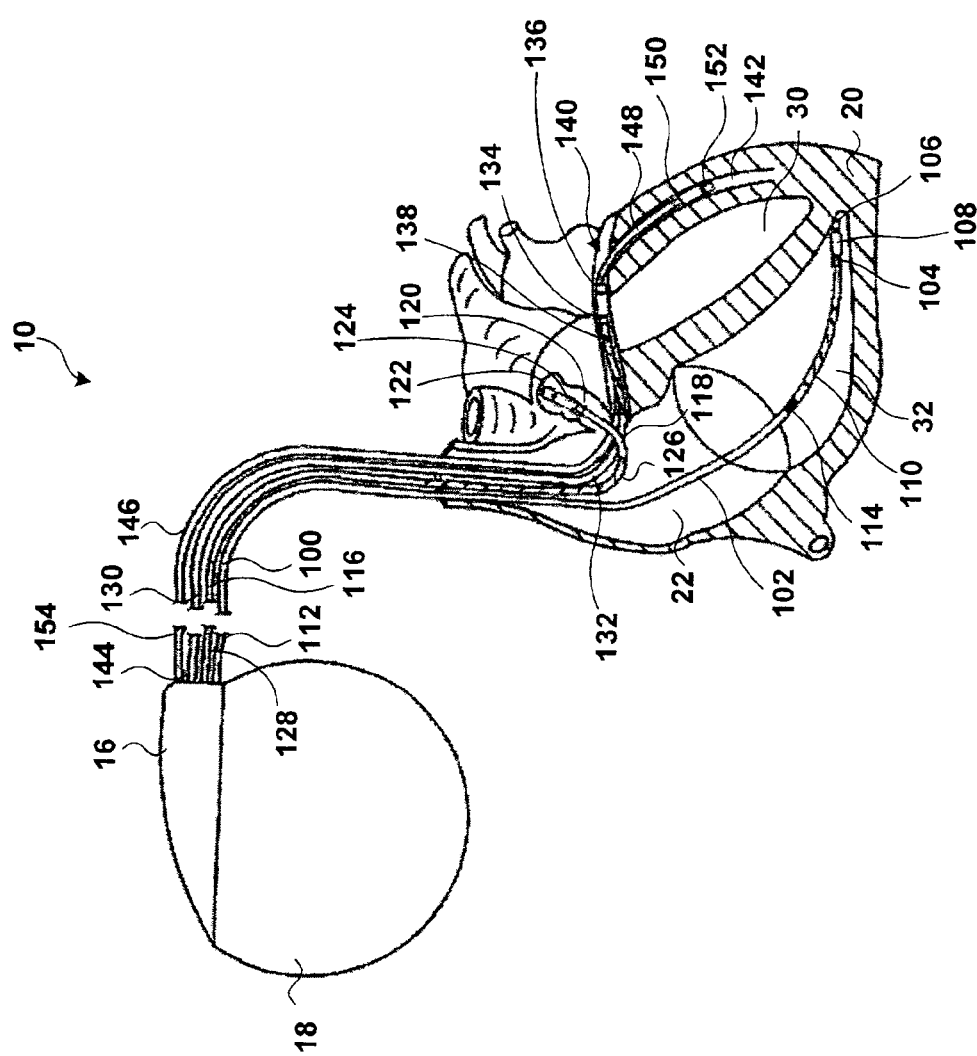
FIG. 4 shows an exemplary implantable multi-chamber medical device located in and near a heart.
Figure 5:
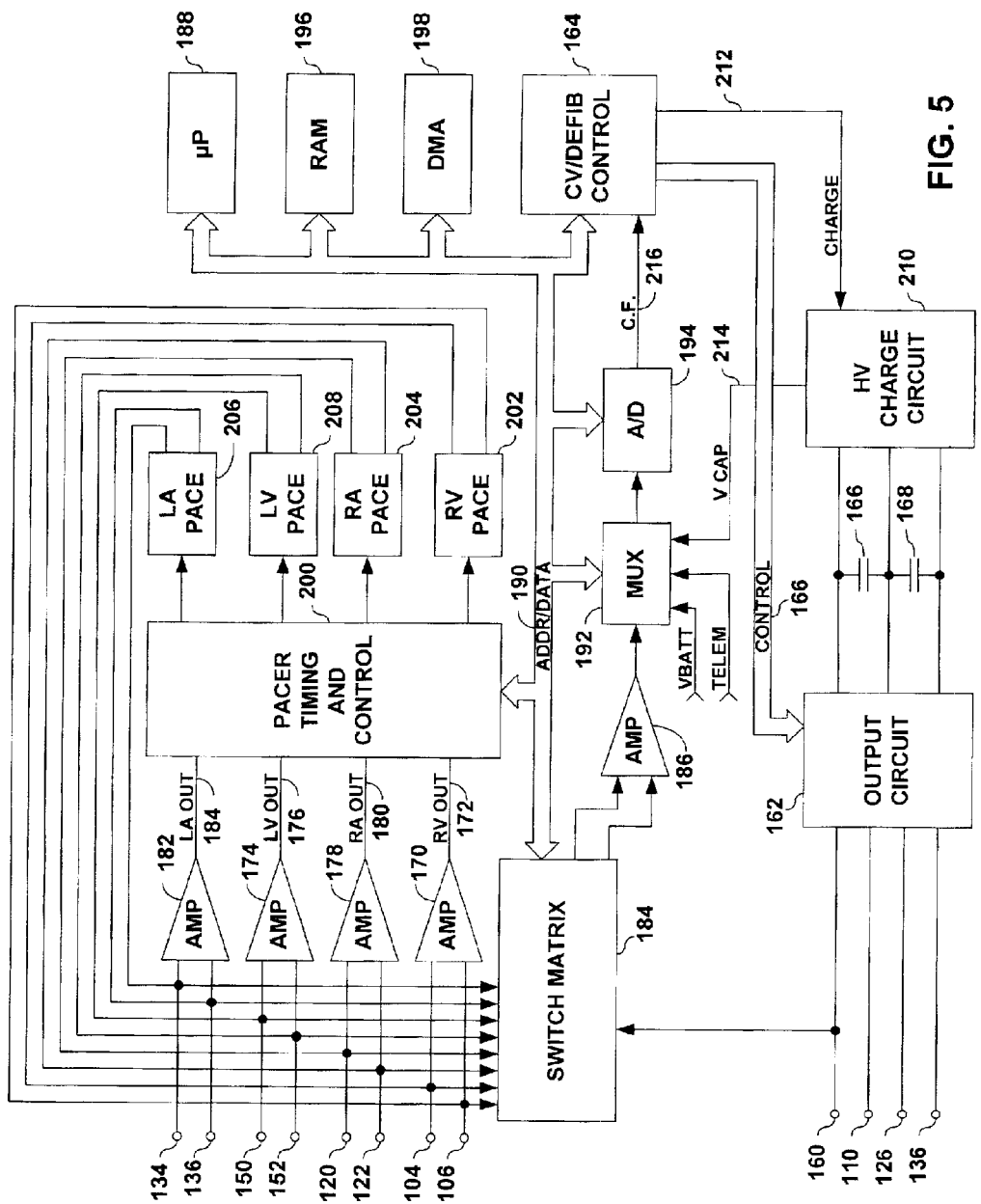
FIG. 5 is a functional schematic diagram of the embodiment of an implantable medical device shown in FIG. 4.

FIGS. 4 and 5 illustrate one embodiment of IMD 10 and a corresponding lead set of the present invention, where IMD 10 is a multi-chamber pacemaker-cardioverter-defibrillator. In FIG. 4, the right ventricular lead 100 may take the form of leads disclosed in U.S. Pat. Nos. 5,099,838 and 5,314,430 to Bardy, and includes an elongated insulative lead body 102 carrying three or more concentric coiled conductors separated from one another by tubular insulative sheaths. Located adjacent the distal end of lead 102 are ring electrode 104, extendable helix electrode 106 mounted retractably within insulative electrode head 108 and elongated coil electrode 110. Each of the electrodes is coupled to one of the coiled conductors within lead body 102. Electrodes 104 and 106 are employed for cardiac pacing and for sensing ventricular depolarizations. At the proximal end of lead 102 is a connector 112 which carries electrical connectors coupled to one of the coiled conductors. Elongated coil electrode 110, which is a defibrillation electrode 110, may be fabricated from platinum, platinum alloy or other materials known to be usable in implantable defibrillation electrodes and may be about 5 cm in length. Lead 100 may also carry a pressure sensor 114, which will be described in more detail below.

The atrial/SVC lead 116 shown in FIG. 4 includes elongated insulative lead body 118 carrying three concentric coiled conductors separated from one another by tubular insulative sheaths corresponding to the structure of ventricular lead 100. Located adjacent the J-shaped distal end of the lead are ring electrode 120 and extendable helix electrode 122 mounted retractably within an insulative electrode head 124. Each of the electrodes is coupled to one of the coiled conductors within lead body 118. Electrodes 122 and 120 are employed for atrial pacing and for sensing atrial depolarizations. Elongated coil electrode 126 is provided proximate to electrode 120 and coupled to the third conductor within lead body 118. Electrode 126 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is connector 128 carrying three electrical connectors, each coupled to one of the coiled conductors.

The coronary sinus lead 130 shown in FIG. 4 assumes the form of a coronary sinus lead disclosed in the above cited '838 patent issued to Bardy, and includes elongated insulative lead body 132 carrying one or more coiled conductors coupled to a ring electrodes 134 and 136 and an elongated coiled defibrillation electrode 138. Electrodes 134, 136 are employed for atrial pacing and for sensing atrial depolarizations. Electrodes 134, 136, 138 are located within the coronary sinus 140 and great vein 142 of heart 20. At the proximal end of the lead 130 is connector plug 144 carrying an electrical connector coupled to the coiled conductor. Elongated coil defibrillation electrode 132 may be about 5 cm in length.

The left ventricular lead 146 may include elongated insulative lead body 148 carrying one or more coiled conductors coupled to a ring electrodes 150 and 152. Electrodes 150, 152 are employed for ventricular pacing and for sensing ventricular depolarizations. Electrodes 150, 152 are located within the great vein 140 of heart 20. At the proximal end of the lead 146 is connector plug 154 carrying an electrical connector coupled to the coiled conductor.

IMD 10 is shown in FIG. 4 in combination with leads 100, 116, 130, 146, and lead connector assemblies 112, 128, 144, 154 inserted into connector module 16. Optionally, insulation of the outward facing portion of housing 18 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 18 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 160 in FIG. 5 includes the uninsulated portion of the housing 18 of IMD 10. Electrodes 110, 126, 136 and 160 are coupled to high voltage output circuit 162, which includes high voltage switches controlled by CV/defib control logic 164 via control bus 166. Switches disposed within circuit 162 determine which electrodes are employed and which electrodes are coupled to the positive and negative terminals of a capacitor bank (which includes capacitors 166 and 168) during delivery of defibrillation pulses.

Electrodes 104 and 106 are located on or in the right ventricle of the patient and are coupled to the R-wave amplifier 170, which preferably takes the form of an automatic gain controlled amplifier providing an adjustable sensing threshold as a function of the measured R-wave amplitude. A signal is generated on R-out line 172 whenever the signal sensed between electrodes 104 and 106 exceeds the present sensing threshold.

Similarly, electrodes 150 and 152 are located proximate to the left ventricle of the patient and are coupled to the R-wave amplifier 174, which preferably also takes the form of an automatic gain controlled amplifier providing an adjustable sensing threshold as a function of the measured R-wave amplitude. A signal is generated on R-out line 176 whenever the signal sensed between electrodes 150 and 152 exceeds the present sensing threshold.

Electrodes 120 and 122 are located on or in the right atrium of the patient and are coupled to the P-wave amplifier 178, which preferably also takes the form of an automatic gain controlled amplifier providing an adjustable sensing threshold as a function of the measured P-wave amplitude. A signal is generated on P-out line 180 whenever the signal sensed between electrodes 120 and 122 exceeds the present sensing threshold.

Similarly, electrodes 134 and 136 are located proximate to the left atrium of the patient and are coupled to the P-wave amplifier 182, which preferably also takes the form of an automatic gain controlled amplifier providing an adjustable sensing threshold as a function of the measured P-wave amplitude. A signal is generated on P-out line 184 whenever the signal sensed between electrodes 134 and 136 exceeds the present sensing threshold. The general operation of R-wave and P-wave amplifiers 170, 174, 178, 182 may correspond to that disclosed in U.S. Pat. No. 5,117,824 to Keimel et al., hereby incorporated by reference herein in its entirety.

Switch matrix 184 is used to select which of the available electrodes are coupled to wide band (0.5–200 Hz) amplifier 186 for use in digital signal analysis. Selection of electrodes is controlled by microprocessor 188 via data/address bus 190, which selections may be varied as desired. Signals from the electrodes selected for coupling to bandpass amplifier 186 are provided to multiplexer 192, and thereafter converted to multi-bit digital signals by A/D converter 194, for storage in random access memory 196 under control of direct memory access circuit 198. Microprocessor 188 may employ digital signal analysis techniques to characterize the digitized signals stored in random access memory 196 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 200 preferably includes programmable digital counters which control the basic time intervals associated with DDD, VVI, DVI, VDD, AAI, DDI and other modes of single and multi-chamber pacing well known to the art. Circuitry 200 also preferably controls escape intervals associated with anti-tachyarrhythmia pacing in both the atrium and the ventricle, employing any anti-tachyarrhythmia pacing therapies known to the art.

Intervals defined by pacing circuitry 200 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 188, in response to stored data in memory 196 and are communicated to pacing circuitry 200 via address/data bus 190. Pacer circuitry 200 also determines the amplitude of the cardiac pacing pulses under control of microprocessor 188.

During pacing, escape interval counters within pacer timing/control circuitry 200 are reset upon sensing of R-waves and P-waves as indicated by a signals on lines 172, 176, 180 and 184 and in accordance with the selected mode of pacing on time-out trigger generation of pacing pulses by pacer output circuitry 202, 204, 206 and 208, which are coupled to electrodes 104, 106, 120, 122, 134, 136, 150 and 152. Escape interval counters are also reset on generation of pacing pulses and thereby control the basic timing of cardiac pacing functions, including anti-tachyarrhythmia pacing. The durations of the intervals defined by escape interval timers are determined by microprocessor 188 via data/ address bus 190. The value of the count present in the escape interval counters when reset by sensed R-waves and P-waves may be used to measure the durations of R-R intervals, P-P intervals, P-R intervals and R-P intervals, which measurements are stored in memory 196 and used to detect the presence of tachyarrhythmias.

Microprocessor 188 most preferably operates as an interrupt driven device, and is responsive to interrupts from pacer timing/control circuitry 200 corresponding to the occurrence of sensed P-waves and R-waves and corresponding to the generation of cardiac pacing pulses. Those interrupts are provided via data/address bus 190. Any necessary mathematical calculations to be performed by microprocessor 188 and any updating of the values or intervals controlled by pacer timing/control circuitry 200 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 188 into the pacer timing and control circuitry 200, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 188 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 188 activates cardioversion/defibrillation control circuitry 164, which initiates charging of high voltage capacitors 166 and 168 via charging circuit 210, under the control of high voltage charging control line 212. The voltage on the high voltage capacitors is monitored via VCAP line 214, which is passed through multiplexer 192 and in response to reaching a predetermined value set by microprocessor 188, results in generation of a logic signal on Cap Full (CF) line 216 to terminate charging. Thereafter, timing of the delivery of the defibrillation or cardioversion pulse is controlled by pacer timing/control circuitry 200. Following delivery of the fibrillation or tachycardia therapy microprocessor 188 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 162 under the control of control circuitry 164 via control bus 166. Output circuit 162 determines whether a monophasic or biphasic pulse is delivered, the polarity of the electrodes and which electrodes are involved in delivery of the pulse. Output circuit 162 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Although FIGS. 4 and 5 depict one electrode per cardiac chamber, the invention is not limited to a single pacing electrode per chamber. Rather, the invention may be applied to multi-chamber pacing in which there maybe two or more electrodes per chamber. For example, the invention may be applied to a bi-ventricular pacing system that includes a single electrode in the right ventricle, but three electrodes placed around the left ventricle, such as the left ventricular anterior-septum wall, the left ventricular lateral free wall, and the left ventricular posterior free wall. Multiple-site electrode placement with respect to a single cardiac chamber may, for some patients, result in more homogenous activation and homogenous mechanical response. Consequently, the invention encompasses embodiments in which a single cardiac chamber is responsive to two or more pacing stimuli.

Similarly, the invention is not limited to a single pressure sensor such as pressure sensor 114. Nor is the invention limited to a single pressure sensor per cardiac chamber. The invention encompasses any number of pressure sensors.

Figure 6:
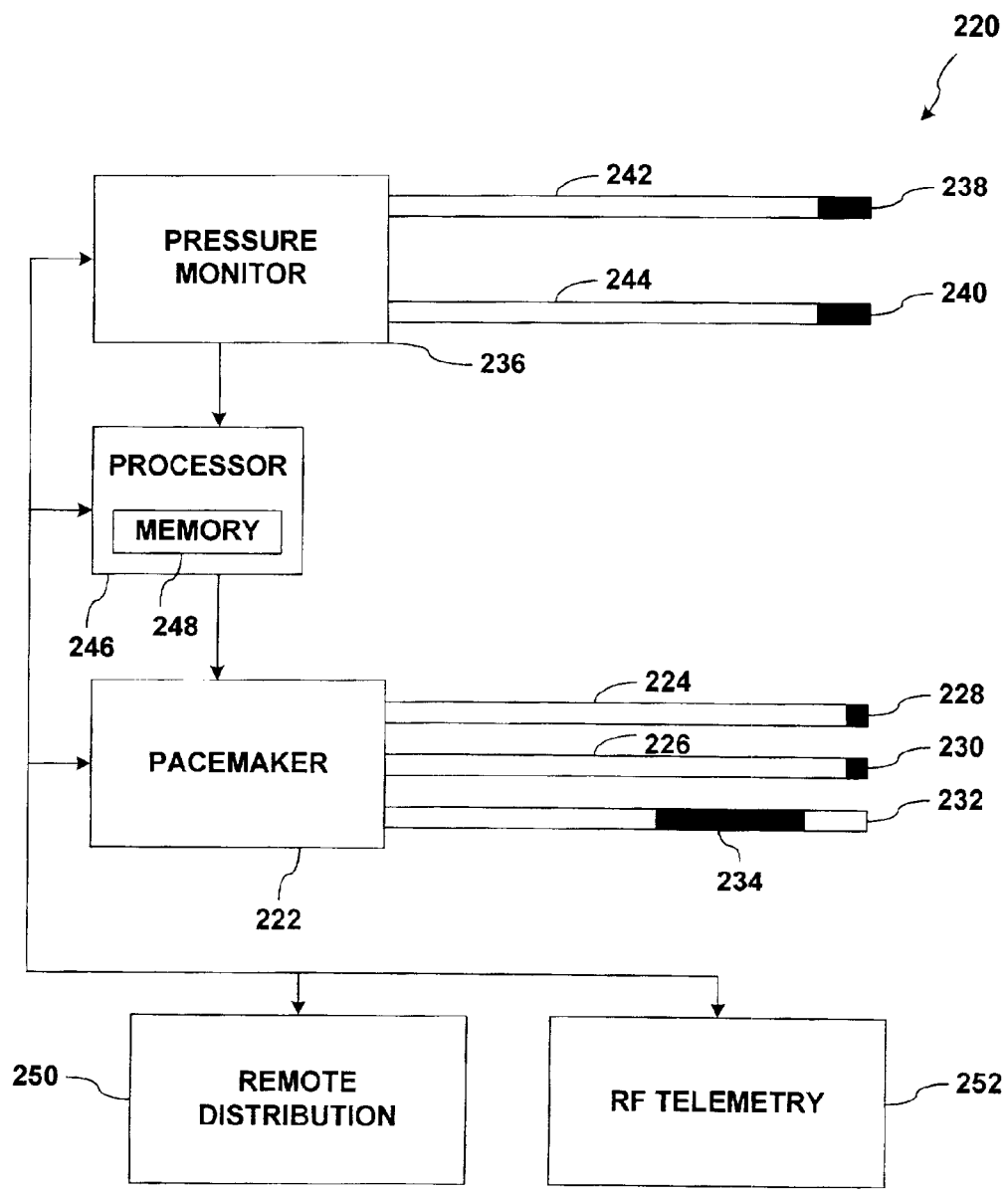
FIG. 6 is a diagram of a system including a pressure monitor and a cardiac pacemaker.

FIG. 6 shows a system 220 illustrating an embodiment of the invention, in which pressure measurements are used to adjust the timing of pacing pulses. System 220, which may be implantable in a human being or a mammal, includes cardiac pacemaker 222. Pacemaker 222 includes a pulse generator that can deliver pacing pulses to two or more chambers of heart 20 (not shown in FIG. 6) using one or more pacing modes. In particular, pacemaker 222 may pace both ventricles, or may pace both atria. In the description of the embodiment that follows, it will be assumed that pacemaker 222 delivers bi-ventricular pacing. It is understood, however, that the invention may also be applied to bi-atrial pacing. The invention may be practiced with the exemplary pacemakers shown in FIGS. 1 through 5, but the invention is not limited to the exemplary pacemakers shown in FIGS. 1 through 5.

Pacemaker 222 may be one of the many forms of implantable medical devices 10 described above, or may be an external pacemaker. Pacemaker 222 may be coupled to leads 224 and 226, which in turn are coupled to electrodes 228 and 230. Electrodes 228 and 230 may correspond to ventricular electrodes 104, 106, 150, 152 described above. Defibrillation coil electrode 234 may correspond to any of elongated coil electrodes 110, 126, 136 described above. The invention is not limited to the exemplary devices and systems shown in FIGS. 1 through 5, however. Defibrillation coil electrode 234 need not have a dedicated lead 232, but may be coupled to lead 224 or 226.

The invention includes techniques for the timing of pacing pulses as a function of the pressure of the blood inside the patient's heart 20. System 220 includes pressure monitor 236, which is coupled to a pressure sensors 238 and 240 by leads 242 and 244. Pressure sensors 238 and 240 need not have dedicated leads, but may be coupled to lead 224 or 226. FIG. 4, for example, shows pressure sensor 114 coupled to right ventricular lead 102.

Pressure sensors 238, 240 may be disposed in ventricles 30, 32. The invention encompasses all techniques for placement of pressure sensors 238, 240. For example, pressure sensors 238, 240 may be disposed on a single lead that descends into right ventricle 32 and penetrates the interventricular septum to left ventricle 30. In another possible configuration, pressure sensor lead 242 may descend into right ventricle 32 and pressure sensor lead 244 may be disposed outside heart 20 and may penetrate the ventricular wall.

Pressure sensors 238, 240 may respond to the absolute pressure inside ventricles 30, 32. Pressure sensors 238, 240 may be, for example, capacitive or piezoelectric absolute pressure sensors. Pressure sensors 238, 240 may generate pressure signals or may modulate pressure signals conducted through leads 242, 244. The pressure signals are a function of the fluid pressure at the site where pressure sensors 238, 240 are disposed. Pressure monitor 236 receives, monitors and analyzes the pressure signals, as will be described in more detail below. An example of pressure monitor 236 is the Chronicle™ Implantable Hemodynamic Monitor manufactured by and commercially available from Medtronic, Inc. of Minneapolis, Minn.

Pacemaker 222 and pressure monitor 236 are coupled to processor 246. Processor 246 is associated with memory 248. Memory 248 may store data such as measured parameters, identified times of cardiac chamber ejection and the results of calculation. Processor 246 is shown as logically separate from pacemaker 222 and pressure monitor 236, but in practice processor 246 may be housed inside pressure monitor 236, or inside pacemaker 222. Processor 246 may be included in microprocessor 188 in the embodiment of implanted medical device 10 shown in FIG. 5, for example. Alternatively, processor 246 may be separate from both pressure monitor 236 and pacemaker 222. Further, pressure monitor 236, pacemaker 222 and processor 246 may be realized as a single implantable device.

Data collected by pacemaker 222, pressure monitor 236 and/or processor 246 may be retrieved via input/output devices such as remote distribution link 250 or RF telemetry 252. Further, pacemaker 222, pressure monitor 236 and/or processor 246 may receive information such as data or programming via input/output devices 250, 252. Remote distribution link 250 may provide a channel for uploading or downloading information over a telephone line or over the internet, for example. RF telemetry 252 may communicate information on a dedicated wireless channel. Typically, a patient is required to visit an office of a physician when information is to be uploaded or downloaded via RF telemetry 252.

Figure 7:
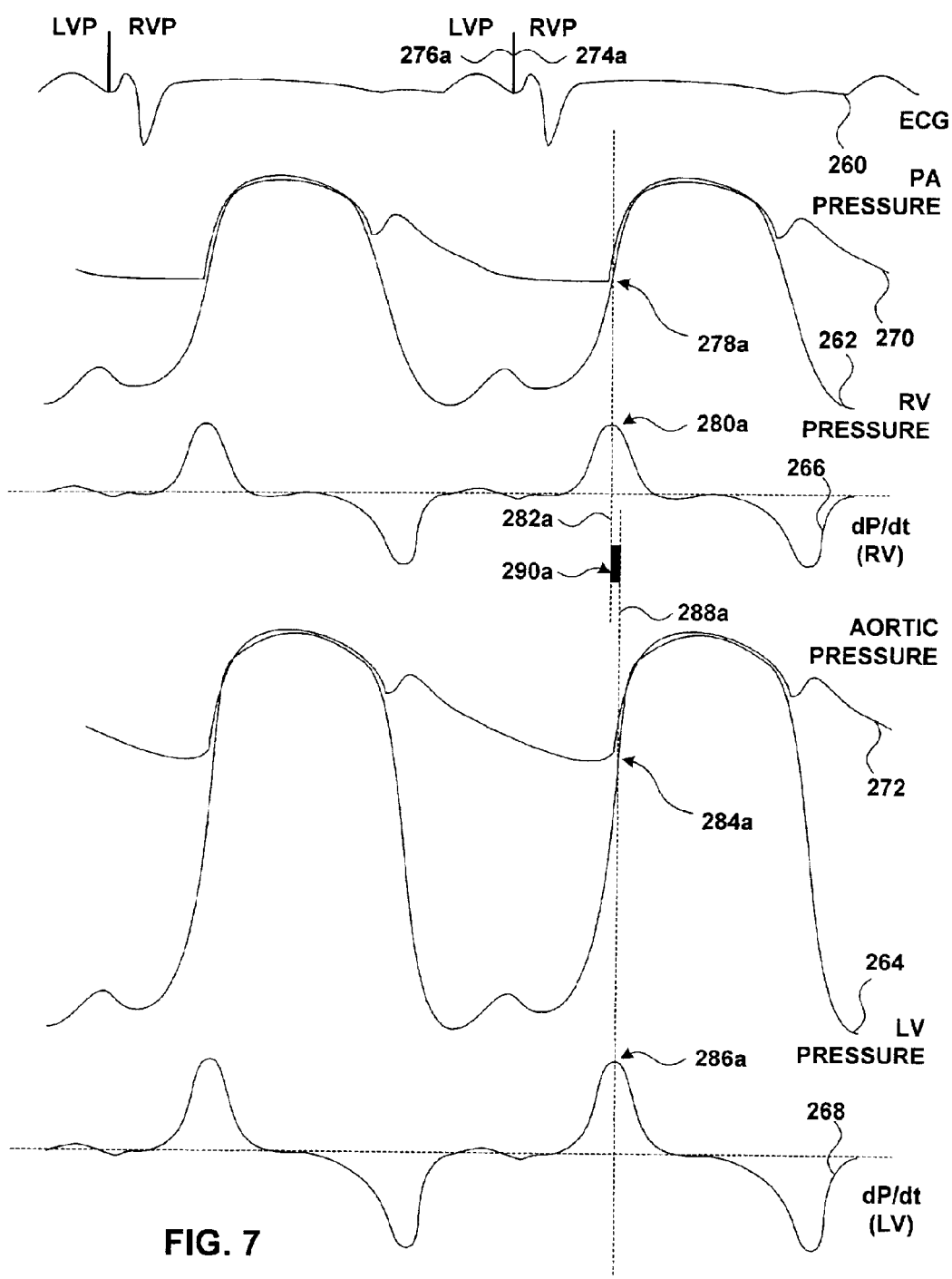
FIG. 7 is a timing diagram illustrating pacing of ventricles with no V1-V2 interval, including an electrocardiogram signal, a corresponding right ventricular pressure signal, a derivative of the right ventricular pressure signal, a corresponding left ventricular pressure signal and a derivative of the left ventricular pressure signal.

FIG. 7 is a timing diagram showing an electrocardiogram (ECG) signal 260, a corresponding right ventricular pressure 262 and a corresponding left ventricular pressure 264. ECG 260 may be sensed by, for example, an electrode on an external electrocardiograph. Right ventricular pressure 262 and left ventricular pressure 264 may be sensed via pressure sensors 238, 240 disposed in ventricles 30, 32.

FIG. 7 also shows the derivative 266 of the right ventricular pressure 262 with respect to time, denoted dP/dt (RV), and the derivative 268 of the left ventricular pressure 264 with respect to time, denoted dP/dt (LV). Derivatives 266, 268 may be computed by pressure monitor 236 or processor 246. FIG. 7 further shows for purposes of reference the pulmonary artery pressure 270 and the aortic pressure 272.

In FIG. 7, a right ventricular pacing pulse (RVP) 274a and a left ventricular pacing pulse (LVP) 276a are delivered simultaneously. RVP 274a and LVP 276a may be delivered by electrodes 228, 230. Pressure data from pressure sensors 238, 240, however, demonstrate that the ventricles are not synchronized, even though the pacing pulses are synchronized.

When a pacing pulse stimulates a cardiac chamber, the chamber does not activate and begin blood ejection instantaneously. Rather, there is an electrical-mechanical delay between the stimulation and ejection. Moreover, the delay between stimulation and ejection is usually different for each chamber of heart 20. The different delays are due to factors such as conductive variations of the chambers and electrode placement proximate to the chambers. In some patients, heart disorders contribute to differences in conduction time and may exacerbate the asynchrony.

The invention is directed to resynchronization of the chambers based upon pressure data from the chambers. In particular, the invention is directed to causing the chambers to begin ejection in a synchronous fashion. In the exemplary embodiments that will be described below, it will be assumed that "ejection in a synchronous fashion" means that the chambers begin ejection at the same time. The invention also encompasses, however, ejection in which the chambers begin ejection at different times, separated by a time delay or "offset."

In FIG. 7, right ventricle 32 begins ejection before left ventricle 30. When right ventricle 32 begins to contract, no blood leaves right ventricle 32 for a short period, and the contraction of right ventricle 32 is isovolumetric. During isovolumetric contraction, the right atrioventricular valve of heart 20 is closed by backward pressure differential forces. The pulmonary valve is likewise closed, as the pressure in right ventricle 32 is insufficient to force blood through the pulmonary valve.

Consequently, isovolumetric contraction causes the blood in right ventricle 32 to undergo increasing pressure. In a short time, the pressure in right ventricle 32 overcomes the pressure in the pulmonary arteries, as reflected in pulmonary artery pressure curve 270, driving the pulmonary valve open, and ejecting blood from right ventricle 32 into the pulmonary arteries. When the pulmonary valve opens, contraction is no longer isovolumetric. Pressure in right ventricle 32, although still increasing due to ventricular contraction, increases at a slower rate. As a result, there is an inflection point 278a in right ventricular pressure curve 262 when the pulmonary valve opens. Inflection point 278a represents the point of maximum change of pressure with time. In right ventricular pressure curve 262, inflection point 278a is the point of maximum slope.

Inflection point 278a may be found by reference to dP/dt (RV) curve 266. Because the slope of pressure signal 262 is at its maximum at inflection point 278a, dP/dt (RV) curve 266 peaks 280a at the same time 282a that inflection point 278a occurs. Inflection point 278a may therefore be found by finding the point on right ventricular pressure curve 262 corresponding to the maximum value of dP/dt (RV) curve 266. Inflection point 278a may also be found by taking the second derivative of right ventricular pressure with respect to time, or $d^2P/dt^2$ (RV) (not shown in FIG. 7) and finding the point on right ventricular pressure curve 262 at which the second derivative curve goes negative for the first time after RVP 274a. This point occurs at the same time 282a that inflection point 278a occurs.

The time at which inflection point 278a occurs is the time 282a that right ventricle 32 begins ejection of blood. By sensing the inflection point or the maximum change in pressure, the time of ejection 282a from right ventricle 32 can be identified.

A similar inflection point 284a may be found for left ventricle 30. In particular, when left ventricle 30 begins to contract, left ventricle 30 undergoes a brief period of isovolumetric contraction. During isovolumetric contraction, the aortic valve is closed. Pressure builds in left ventricle 30 until the pressure in left ventricle 30 overcomes the pressure in the aorta as illustrated by aortic pressure curve 272. At this point, left ventricular pressure drives open the aortic valve, ejecting blood into the aorta.

Like right ventricle 32, isovolumetric contraction in left ventricle 30 ends when blood ejection begins. Pressure in left ventricle 30, although still increasing due to ventricular contraction, increases at a slower rate. As a result, there is an inflection point 284a in left ventricular pressure curve 264 when the aortic valve opens.

Inflection point 284a in left ventricular pressure curve 264 may be found using techniques similar to those used to find inflection point 278a in right ventricular pressure curve 262. For example, the time of inflection point 284a may be found by reference to dP/dt (LV) curve 268, particularly the maximum value 286a on dP/dt (LV) curve 268. In this way, the time 288a that left ventricle 30 begins ejection of blood can be identified.

Ejection from right ventricle 32 begins at time 282a. Ejection from left ventricle 30 begins at time 288a. As FIG. 7 shows, there is a delay 290a between the times of ejection 288a, 282a from left and right ventricles 30, 32, with right ventricle 32 beginning ejection first. For purposes of illustration of the invention, it will be assumed that delay 290a represents an undesirable asynchrony between ventricles 30, 32. It will also be assumed that, for this patient, simultaneous ejection from ventricles 30, 32 is desirable and that the hemodynamic functions of the heart are optimized when simultaneous ejection occurs.

Figure 8:
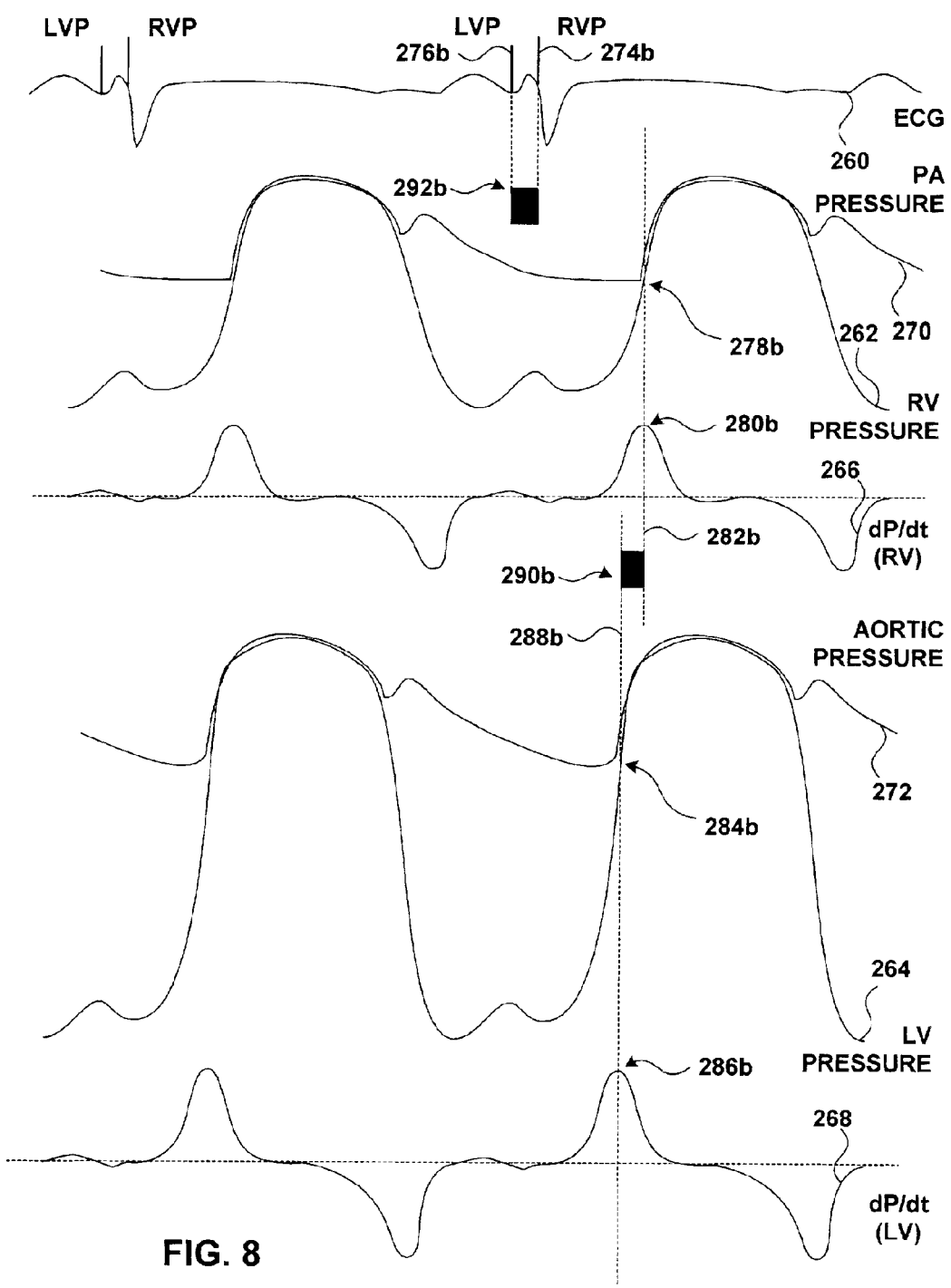
FIG. 8 is a timing diagram similar to FIG. 7, illustrating pacing of ventricles with a V1-V2 interval that results in asynchrony.

FIG. 8 is a timing diagram that, like FIG. 7, shows ECG signal 260, the corresponding right ventricular pressure 262 and the corresponding left ventricular pressure 264, along with the pressure derivative curves 266, 268. Unlike FIG. 7, however, RVP 274b and LVP 276b are not delivered simultaneously. Instead, pacemaker 222 delivers LVP 276b prior to RVP 274b. FIG. 8 shows a V1-V2 interval 292b that represents the delay between the delivery of LVP 276b and RVP 274b.

In FIG. 8, left ventricle 30 begins ejection before right ventricle 32. The time of left ventricular ejection 288b and right ventricular ejection 282b may be determined using the analysis described above. In particular, the times of ejection 282b, 288b for each ventricle may be identified by, for example, finding inflection points 278b, 284b and/or peaks 280b, 286b of pressure derivative curves 266, 268. As FIG. 8 shows, there is a delay 290b between the times of ejection from left and right ventricles 30, 32, with left ventricle 30 beginning ejection first. Delay 290b, like delay 290a in FIG. 7, represents an undesirable asynchrony between ventricles 30, 32. FIG. 8 illustrates that, like the synchronous pacing shown in FIG. 7, pacing with a V1-V2 interval 292b can result in undesirable asynchrony.

Figure 9:
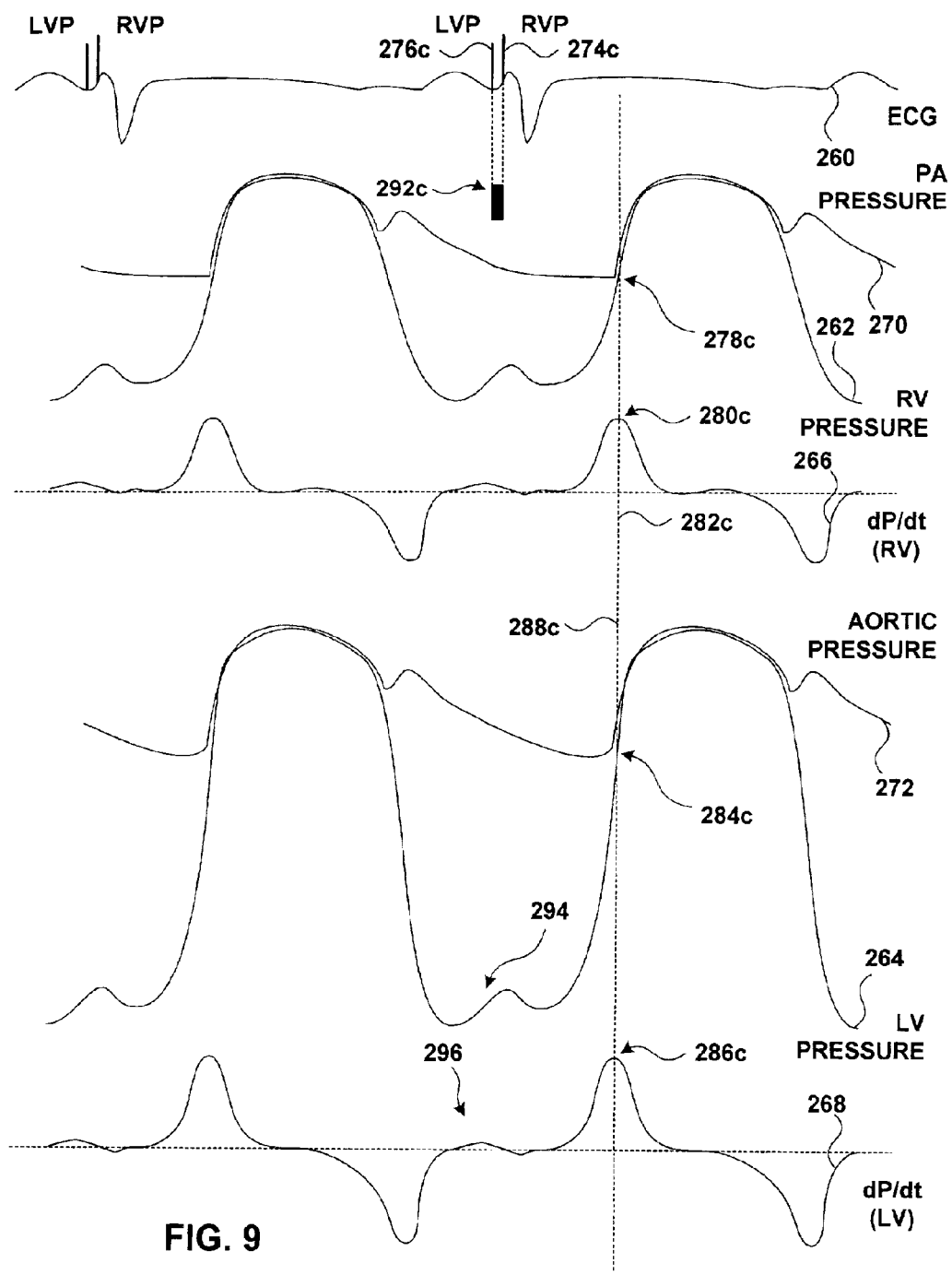
FIG. 9 is a timing diagram similar to FIG. 7, illustrating pacing of ventricles with a V1-V2 interval that results in synchrony.

FIG. 9 is a timing diagram that illustrates use of a V1-V2 interval 292c that results in synchrony of ejection. FIG. 9, like FIGS. 7 and 8, shows ECG signal 260, the corresponding right ventricular pressure 262 and the corresponding left ventricular pressure 264, along with the pressure derivative curves 266, 268. Pacemaker 222 delivers LVP 276c, and following V1-V2 interval 292c, pacemaker 22 delivers RVP 274c.

When paced with V1-V2 interval 292c, the time of left ventricular ejection 288c coincides with the time of right ventricular ejection 282c. The ejection times 282c, 288c may be determined using the analysis described above.

Because the ejection times are synchronized, there is no undesirable delay like delays 290*a* and 290*b* in FIGS. 7 and 8. Ventricles 30, 32 are synchronized to eject blood at the same time, which is a desirable result for this patient.

It is important to note that a patient's physician may deem asynchronous ventricular ejection to be desirable in some patients. It is possible, for example, that the cardiac output of the heart of a particular patient may be optimized by causing one ventricle to begin ejecting blood before the other. In other words, ejection offsets such as delays 290*a* and 290*b* may be desirable in some patients. The invention can be applied for the benefit of such patients. In particular, the techniques of the invention can be applied to cause ventricles 30, 32 to eject in any order, with any ejection offset. The time of left ventricular ejection and right ventricular ejection may be determined using the techniques described above, and the V1-V2 interval may be adjusted to produce asynchronous ejection with a desired offset.

Although the invention is applicable to bi-ventricular pacing, the techniques of the invention may also be applied to bi-atrial pacing. In particular, pressure data from the ventricles and/or from the atria may be used to resynchronize atrial contractions. In FIG. 9, for example, a sharp rise 294 in left ventricular pressure curve 264 indicates the onset of left atrial contraction, and the onset of atrial contraction may be reflected 296 in dP/dt (LV) curve 268 as well. Alternatively, pressure sensors in the atria may be used to detect atrial contractions by detecting the pressure change that accompanies contraction. The invention encompasses adjusting A1-A2 intervals to resynchronize atrial contractions. The invention further encompasses adjusting A1-A2 and V1-V2 intervals in bi-atrial and bi-ventricular pacing performed with a multi-chamber device such as device 10 depicted in FIGS. 4 and 5.

FIG. 10 illustrates exemplary techniques for adjusting the V1-V2 interval to produce synchronous ventricular ejection, if desired, or ventricular ejection with a desired offset. System 220 receives a desired offset (300) as a parameter. An offset of zero may signify that synchronous ventricular ejection is desired. A physician, for example, may program the offset via input/output devices 250, 252. It is also possible that the offset may be selected as a function of measured data, such as measured cardiac output, without direct intervention by the physician.

In one embodiment of the invention, pacemaker 222 delivers simultaneous pacing pulses to ventricles 30, 32, i.e., pacemaker 222 delivers pacing pulses with a V1-V2 interval is equal to zero (302). It is not necessary to the invention that the initial V1-V2 interval be zero. The V1-V2 interval may be any known time interval, and the invention encompasses all initial V1-V2 intervals.

Pressure monitor 236 and processor 246 may cooperate to identify the times that left ventricle 30 and right ventricle 32 commence ejection, using the techniques described above, and compute the delay between ejection times (306). By comparison of the delay to the desired offset (308), processor 246 may adjust the V1-V2 interval to cause ventricles 30, 32 to commence ejection with the desired offset (310). In particular, processor 246 may introduce a V1-V2 interval equal in magnitude to the difference between the actual delay and the desired offset.

Pacing with the initial V1-V2 interval (302) and identification of ejection times (304) may be performed during a single cardiac cycle. In subsequent cardiac cycles, ventricles 30, 32 may be paced with the adjusted interval (312).

The techniques may be repeated with the adjusted V1-V2 interval (314) to determine whether the desired offset has been achieved. Moreover, the techniques may be repeated (314) on a periodic basis to monitor cardiac performance and to determine whether another adjustment to the V1-V2 interval is indicated.

The techniques may also be repeated (314) in response to a change in cardiac conditions, such as a change in heart rate due to increased patient activity. A change in heart rate may cause changes to the conductive qualities of the cardiac tissue. As a result, a V1-V2 interval at one heart rate may result in efficient synchrony, but the same V1-V2 interval at a higher heart rate may result in less efficient pumping. The invention encompasses adjustment to the V1-V2 interval to maintain good hemodynamic performance when cardiac conditions change.

Although the techniques described in FIG. 10 are applicable to bi-ventricular pacing, the techniques may also be applied to bi-atrial pacing. In particular, pressure data from the atria or the ventricles may be used to select an A1-A2 interval that synchronizes atrial ejection into the ventricles. In addition, the techniques may be applied to adjust A1-A2 and V1-V2 intervals in a patient having a multi-chamber pacemaker.

The invention offers several advantages. In patients receiving bi-ventricular pacing, bi-atrial pacing or both bi-ventricular and bi-atrial pacing, the invention promotes the hemodynamic performance of the heart by adjusting pacing intervals to achieve the best results for the patient. The intervals may be adjusted automatically in response to changes in conditions, such as a change in heart rate or a change in the conductive pathways of the heart.

Further, the invention can be adapted to a variety of devices. Bi-ventricular, bi-atrial, three-chamber and four-chamber devices may apply the techniques described above to resynchronize the heart. Moreover, the invention can be adapted to any configuration of electrode placements and is not limited to the electrode placements depicted in FIGS. 2 and 4. Nor is the invention limited to any particular technique for pressure sensor placement.

The preceding specific embodiments are illustrative of the practice of the invention. It is to be understood, therefore, that other expedients known to those skilled in the art or disclosed herein may be employed without departing from the invention or the scope of the claims. For example, the techniques of the invention may be employed to synchronize other features of the cardiac cycle. As described above, the invention adjusts V1-V2 and/or A1-A2 intervals to synchronize ejection time, but the invention is not limited to synchronization of ejection time.

The invention may be applied, for example, to synchronization of peak pressures, which may be identified with reference to zero crossings in derivative pressure curves 266 and 268. Another application may synchronize peak relaxation period. This application may be realized by finding the point on pressure curves 262, 264 corresponding to the minimum values of dP/dt curve 266, 268. The application may also be realized by taking the second derivative of ventricular pressures with respect to time (not shown in FIGS. 7–9), and finding the points on ventricular pressure curves 262 and 264 at which the second derivative curve goes positive after delivery of a corresponding ventricular pacing pulse and peak dP/dt. Other events on the pressure curves 262, 264, first derivative curves 266, 268, or other derived curves may be used for synchronization. Although ejection times are, in general, easier to identify and are more directly indicative of cardiac performance than other events, the invention is not limited to synchronization of ejection times.

The invention further includes within its scope the methods of making and using the systems described above. These methods are not limited to the specific examples described above, but may be adapted to meet the needs of a particular patient. The invention also includes within its scope any of computer-readable media comprising instructions for causing a programmable processor, such as microprocessor, to carry out the techniques described above. Such computer-readable media include, but are not limited to, magnetic and optical storage media, and read-only memory such as erasable programmable read-only memory or flash memory accessible by the processor. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device system comprising:
   a pulse generator that delivers a first pacing pulse to a first ventricle and a second pacing pulse to a second ventricle following a pacing interval;
   a pressure monitor that monitors a pressure fluctuation within the first ventricle and a pressure fluctuation within the second ventricle; and
   a processor that adjusts the pacing interval as a function of the pressure fluctuation within the first ventricle and the pressure fluctuation within the second ventricle.

2. The system of claim 1, wherein:
   the pulse generator delivers the first pacing pulse to the first ventricle and the second pacing pulse to the second ventricle during a cardiac cycle;
   the pressure monitor monitors the pressure in the first ventricle and the pressure in the second ventricle during the cardiac cycle;
   the pulse generator delivers a third pacing pulse to one of the first ventricle and the second ventricle during a subsequent cardiac cycle; and
   the pulse generator delivers a fourth pacing pulse, following the third pacing pulse and the pacing interval, to the other of the first ventricle and the second ventricle during the subsequent cardiac cycle.

3. The system of claim 1, wherein the pacing interval between delivery of the first pacing pulse and delivery of the second pacing pulse is zero.

4. The system of claim 1, wherein at least one of the pressure monitor and the processor:
   identifies a first time at which a maximum change of pressure in the first ventricle occurs; and
   identifies a second time at which a maximum change of pressure in the second ventricle occurs.

5. The system of claim 4, wherein the processor adjusts the pacing interval to cause, in a subsequent cardiac cycle, a third time at which the maximum change of pressure in the first ventricle occurs to be the same as a fourth time at which the maximum change of pressure in the second ventricle occurs.

6. The system of claim 4, wherein the processor adjusts the pacing interval to cause, in a subsequent cardiac cycle, a third time at which the maximum change of pressure in the first ventricle occurs to precede by an offset time a fourth time at which the maximum change of pressure in the second ventricle occurs.

7. The system of claim 1, wherein at least one of the pressure monitor and the processor:
   generates a first signal that is a derivative of the pressure in the first ventricle;
   generates a second signal that is a derivative of the pressure in the second ventricle;
   identifies a first time at which the first signal reaches a first maximum; and
   identifies a second time at which the second signal reaches a second maximum.

8. The system of claim 7, wherein the processor adjusts the pacing interval to cause, in a subsequent cardiac cycle, a third time at which the first signal reaches a third maximum to be the same as a fourth time at which the second signal reaches a fourth maximum.

9. The system of claim 1, wherein at least one of the pressure monitor and the processor:
   identifies a first time at which the first ventricle commences ejection of blood; and
   identifies a second time at which the second ventricle commences ejection of blood.

10. The system of claim 9, wherein the processor adjusts the pacing interval to cause, in a subsequent cardiac cycle, a third time at which the first ventricle commences ejection of blood to be the same as a fourth time at which the second ventricle commences ejection of blood.

11. The system of claim 1, further comprising:
    a first pressure sensor coupled to the pressure monitor, the first pressure sensor disposed in the first ventricle; and
    a second pressure sensor coupled to the pressure monitor, the second pressure sensor disposed in the second ventricle.

12. The system of claim 1, further comprising:
    a first electrode coupled to the pulse generator for delivery of the first pacing pulse, the first electrode disposed proximate to the first ventricle; and
    a second electrode coupled to the pulse generator for delivery of the second pacing pulse, the second electrode disposed proximate to the second ventricle.

13. The system of claim 12, further comprising a third electrode coupled to the pulse generator, the third electrode disposed proximate to the first ventricle.

14. The system of claim 1, wherein the pulse generator, pressure monitor and processor are included in a single implantable device.

15. A method comprising:
    identifying a first time when a first ventricle of a heart commences ejection of blood in response to a first pacing pulse;
    identifying a second time when a second ventricle of the heart commences ejection of blood in response to a second pacing pulse;
    setting a pacing interval as function of the first time and the second time.

16. The method of claim 15, further comprising:
    monitoring a first pressure in the first ventricle;
    identifying the first time as a function of the first pressure;
    monitoring a second pressure in the second ventricle; and
    identifying the second time as a function of the second pressure.

17. The method of claim 15, further comprising:
delivering the first pacing pulse b the first ventricle; and
delivering the second pacing pulse to the second ventricle.

18. The method of claim 15, further comprising:
delivering a third pacing pulse to one of the first and the second ventricle; and
delivering a fourth pacing pulse after the third pacing pulse and the pacing interval to the other of the first and the second ventricle.

19. The method of claim 15, wherein the pacing interval is a second pacing interval, the method further comprising delivering the second pacing pulse to the second ventricle after the first pacing pulse and a first pacing interval.

20. The method of claim 15, further comprising delivering the first pacing pulse and the second pacing pulse simultaneously.

21. The method of claim 15, further comprising setting the pacing interval to cause, in a subsequent cardiac cycle, a third time at which the first ventricle commences ejection of blood to be the same as a fourth time at which the second ventricle commences ejection of blood.

22. The method of claim 15, wherein setting the pacing interval comprises adjusting a previous pacing interval.

23. The method of claim 15, further comprising computing the delay between the first time and the second time.

24. The method of claim 23, further comprising setting the pacing interval as function of the computed delay.

25. The method of claim 23, further comprising setting the pacing interval as function of the computed delay and as a function of a desired offset delay.

26. The method of claim 15, further comprising receiving an offset delay.

27. The method of claim 15, wherein the first ventricle receives a third pacing pulse, and
wherein identifying the first time comprises identifying a time when the first ventricle commences ejection of blood in response to the first and third pacing pulses.

28. A computer-readable medium comprising instructions that cause a processor to:
identify a first time when a first ventricle of a heart commences ejection of blood in response to a first pacing pulse;
identify a second time when a second ventricle of the heart commences ejection of blood in response to a second pacing pulse;
set a pacing interval as function of the first time and the second time.

29. The medium of claim 28, the instructions further causing the processor to:
monitor a first pressure in the first ventricle;
identify the first time as a function of the first pressure;
monitor a second pressure in the second ventricle; and
identify the second time as a function of the second pressure.

30. The medium of claim 28, the instructions further causing the processor to:
deliver the first pacing pulse to the first ventricle; and
deliver the second pacing pulse to the second ventricle.

31. The medium of claim 28, the instructions further causing the processor to:
deliver a third pacing pulse to one of the first and the second ventricle; and
deliver a fourth pacing pulse after the third pacing pulse and the pacing interval to the other of the first and the second ventricle.

32. The medium of claim 28, wherein the pacing interval is a second pacing interval, the method further comprising delivering the second pacing pulse to the second ventricle after the first pacing pulse and a first pacing interval.

33. The medium of claim 28, the instructions further causing the processor to deliver the first pacing pulse and the second pacing pulse simultaneously.

34. The medium of claim 28, the instructions further causing the processor to set the pacing interval to cause, in a subsequent cardiac cycle, a third time at which the first ventricle commences ejection of blood to be the same as a fourth time at which the second ventricle commences ejection of blood.

35. The medium of claim 28, wherein setting the pacing interval comprises adjusting a previous pacing interval.

36. The medium of claim 28, the instructions further causing the processor to compute the delay between the first time and the second time.

37. The medium of claim 36, the instructions further causing the processor to set the pacing interval as function of the computed delay.

38. The medium of claim 36, the instructions further causing the processor to set the pacing interval as function of the computed delay and as a function of a desired offset delay.

39. The medium of claim 28, the instructions further causing the processor to receive an offset delay.

40. The medium of claim 28, wherein the first ventricle receives a third pacing pulse, and
wherein identifying the first time comprises identifying a time when the first ventricle commences ejection of blood in response to the first and third pacing pulses.

41. An implantable medical device system comprising:
a pulse generator that delivers a first pacing pulse to a first atrium and a second pacing pulse to a second atrium following a pacing interval;
a pressure monitor that monitors a pressure in a first cardiac chamber and a pressure in a second cardiac chamber; and
a processor that adjusts the pacing interval as a function of the pressure in the first cardiac chamber end the pressure in the second cardiac chamber.

42. The system of claim 41, wherein the first cardiac chamber is the first atrium and the second cardiac chamber is the second atrium.

43. The system of claim 41, wherein:
the pulse generator delivers the first pacing pulse to the first atrium and the second pacing pulse to the second atrium during a first cardiac cycle;
the pressure monitor monitors the pressure in the first cardiac chamber and the pressure in the second cardiac chamber during the first cardiac cycle;
the pulse generator delivers a third pacing pulse to one of the first atrium and the second atrium during a second cardiac cycle; and
the pulse generator delivers a fourth pacing pulse, following the third pacing pulse and the pacing interval, to the other of the first atrium and the second atrium during the second cardiac cycle.

44. The system of claim 41, wherein the pacing interval between delivery of the first pacing pulse and delivery of the second pacing pulse is zero.

45. The system of claim 41, further comprising:
a first pressure sensor coupled to the pressure monitor, the first pressure sensor disposed in the first cardiac chamber, and a second pressure sensor coupled to the pressure monitor, the second pressure sensor disposed in the second cardiac chamber.

46. The system of claim 41, further comprising:

a first electrode coupled to the pulse generator for delivery of the first pacing pulse, the first electrode disposed proximate to the first atrium; and a second electrode coupled to the pulse generator for delivery of the second pacing pulse, the second electrode disposed proximate to the second atrium.

47. The system of claim 46, further comprising a third electrode coupled to the pulse generator, the third electrode disposed proximate to the first atrium.

48. The system of claim 41, wherein the pulse generator, pressure monitor and processor are included in a single implantable device.

49. A method comprising:

identifying a first time when a first atrium of a heart contracts in response to a first pacing pulse;

identifying a second time when a second atrium of the heart contracts in response to a second pacing pulse;

setting a pacing interval as function of the first time and the second time.

50. The method of claim 49, further comprising:

delivering the first pacing pulse to the first atrium ; and delivering the second pacing pulse to the second atrium.

51. The method of claim 49, further comprising:

monitoring a first pressure in a first cardiac chamber; and monitoring a second pressure in a second cardiac chamber, wherein the first time is identified as a function of the first monitored pressure and the second time is identified as a function of the second monitored pressure.

52. The method of claim 49, wherein the first atrium receives a third pacing pulse, and wherein identifying the first time comprises identifying a time when the first atrium commences ejection of blood in response to the first and third pacing pulses.

53. An implantable medical device system comprising:

means for delivering pacing pulses to two complementary cardiac chambers of a heart, wherein complementary cardiac chambers comprise one of two ventricles and two atria, and wherein the pacing pulses are separated by an interval;

means for monitoring the pressure fluctuation within each of the complementary cardiac chambers; and means for adjusting the interval as a function of the monitored pressures.

54. The system of claim 53, further comprising:

means for identifying a first time when a first ventricle of the heart commences ejection of blood in response to a first pacing pulse; and means for identifying a second time when a second ventricle commences ejection of blood in response to a second pacing pulse.

55. The system of claim 54, wherein the means for adjusting the interval adjusts the interval as a function of the first time and the second time.

56. The system of claim 53, further comprising:

first means for sensing pressure in one of the complementary cardiac chambers; and second means for sensing pressure in the other of the complementary cardiac chambers.

57. The system of claim 56, further comprising third means for sensing pressure in the one of the complementary cardiac chambers.

58. The system of claim 53, further comprising:

first means for delivering a pacing pulse to one of the complementary cardiac chambers; and second means for delivering a pacing pulse to the other of the complementary cardiac chambers.

59. The system of claim 58, further comprising third means for delivering a pacing pulse to the one of the complementary cardiac chambers.

60. An implantable medical device comprising:

a pulse generator that applies a first pacing pulse to a first ventricle of a heart and a second pacing pulse to a second ventricle of a heart following an interval;

a controller that controls the pulse generator to deliver the first pacing pulse and the second pacing pulse following the interval, wherein the interval is a function of a first pressure measured within the first ventricle and a second pressure measured within the second ventricle.

61. The device of claim 60, further comprising a pressure monitor that monitors the first pressure in the first ventricle and a second pressure in the second ventricle.

62. The device of claim 61, wherein the pressure monitor identifies a first time at which the first ventricle commences ejection of blood and identifies a second time at which the second ventricle commences ejection of blood.

63. The device of claim 61, further comprising a first pressure sensor disposed in the first ventricle coupled to the pressure monitor and a second pressure sensor disposed in the second ventricle coupled to the pressure monitor.

* * * * *

UNITED STATES PATENT AND TRADEMARK OFFICE
CERTIFICATE OF CORRECTION

PATENT NO. : 6,934,586 B2
APPLICATION NO. : 10/127037
DATED : August 23, 2005
INVENTOR(S) : Struble et al.

Page 1 of 1

It is certified that error appears in the above-identified patent and that said Letters Patent is hereby corrected as shown below:

Col. 21, line 2, please delete "pulse b the" and insert --pulse to the--

Col. 22, line 41, please delete "chamber end" and insert --chamber and--

Signed and Sealed this

Twentieth Day of March, 2007

JON W. DUDAS
*Director of the United States Patent and Trademark Office*